United States Patent
Kellum, Jr. et al.

(10) Patent No.: US 10,322,221 B2
(45) Date of Patent: Jun. 18, 2019

(54) REMOVAL OF CARBON DIOXIDE VIA DIALYSIS

(71) Applicant: University of Pittsburgh—Of the Commonwealth System of Higher Education, Pittsburgh, PA (US)

(72) Inventors: John Alston Kellum, Jr., Pittsburgh, PA (US); Matthew Cove, Singapore (SG); William J. Federspiel, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 212 days.

(21) Appl. No.: 14/761,321

(22) PCT Filed: Jan. 18, 2014

(86) PCT No.: PCT/US2014/012151
§ 371 (c)(1),
(2) Date: Jul. 16, 2015

(87) PCT Pub. No.: WO2014/113740
PCT Pub. Date: Jul. 24, 2014

(65) Prior Publication Data
US 2015/0335807 A1    Nov. 26, 2015

Related U.S. Application Data

(60) Provisional application No. 61/754,435, filed on Jan. 18, 2013.

(51) Int. Cl.
*A61M 1/16* (2006.01)
*B01D 61/24* (2006.01)
*B01D 63/02* (2006.01)

(52) U.S. Cl.
CPC ........ *A61M 1/1654* (2013.01); *A61M 1/1694* (2013.01); *A61M 1/1698* (2013.01);
(Continued)

(58) Field of Classification Search
CPC .............. A61M 1/3465; A61M 1/3621; A61M 1/3627; A61M 1/14; A61M 1/287
See application file for complete search history.

(56) References Cited

U.S. PATENT DOCUMENTS 3,910,780 A   10/1975 Henley
4,073,686 A   2/1978 Adams
(Continued)

FOREIGN PATENT DOCUMENTS

GB    1220284       1/1971
WO    WO9855210    12/1998
(Continued)

OTHER PUBLICATIONS

Sen et al. 209: Extracorporeal Carbondioxide Removal by Zero Bicarbonate Dialysate: A Novel Lung Protection Strategy, Critical Care Medicine, 2013, vol. 41, No. 12, A47 (2013).
(Continued)

*Primary Examiner* — Ana M Fortuna
(74) *Attorney, Agent, or Firm* — Bartony & Associates, LLC.

(57) ABSTRACT

A method of reducing the concentration of carbon dioxide in blood plasma includes removing blood from a patient and treating or processing at least blood plasma of the blood by flowing the blood plasma on one side of at least one semi-permeable membrane and flowing a dialysate on the other side of the at least one semi-permeable membrane. The dialysate has a concentration of bicarbonate less than the concentration of bicarbonate in the blood plasma before treating the blood plasma and has a composition such that
(Continued)

the blood plasma strong ion difference that results from treating the blood plasma in conjunction with an achieved reduction in blood plasma CO2 concentration results in a blood plasma pH that does not change by more than +/−0.5 during treatment.

16 Claims, 6 Drawing Sheets

(52) U.S. Cl.
CPC ............ *B01D 61/24* (2013.01); *A61M 1/1613* (2014.02); *A61M 2230/202* (2013.01); *A61M 2230/208* (2013.01); *B01D 63/02* (2013.01); *B01D 2311/13* (2013.01)

(56) References Cited

U.S. PATENT DOCUMENTS

| | | | |
|---|---|---|---|
| 4,112,052 A | 9/1978 | Sartori | |
| 4,602,987 A | 7/1986 | Bonaventura | |
| 4,761,209 A | 8/1988 | Bonaventura | |
| 5,132,108 A | 7/1992 | Narayanan | |
| 5,143,847 A | 9/1992 | Kawase | |
| 5,482,996 A | 1/1996 | Russell | |
| 5,614,378 A | 3/1997 | Yang | |
| 6,143,556 A | 11/2000 | Trachtenberg | |
| 6,203,599 B1 | 3/2001 | Schubert | |
| 6,524,843 B1 | 2/2003 | Blais | |
| 6,946,288 B2 | 9/2005 | Blais | |
| 7,763,097 B2* | 7/2010 | Federspiel | A61M 1/1698 210/500.21 |
| 7,909,788 B2 | 3/2011 | Monzyk | |
| 7,927,544 B2 | 4/2011 | Feberspiel | |
| 8,034,161 B2 | 10/2011 | Gura | |
| 8,043,411 B2 | 10/2011 | Federspiel | |
| 9,399,090 B2* | 7/2016 | Collier | A61M 1/1654 |
| 2003/0010701 A1 | 1/2003 | Collins | |
| 2004/0029257 A1 | 2/2004 | Dutil | |
| 2004/0060865 A1* | 4/2004 | Callan | A61K 31/19 210/646 |
| 2004/0219090 A1 | 11/2004 | Dziedzic | |
| 2004/0259231 A1 | 12/2004 | Bhattacharya | |
| 2005/0119598 A1* | 6/2005 | Callan | A61K 31/19 604/5.01 |
| 2006/0014172 A1 | 1/2006 | Muller | |
| 2006/0201874 A1 | 9/2006 | Klare | |
| 2006/0263904 A1 | 11/2006 | Morozou | |
| 2010/0170849 A1* | 7/2010 | Callan | A61K 31/19 210/645 |
| 2010/0198132 A1* | 8/2010 | Pesenti | A61M 1/1698 604/6.09 |
| 2012/0035523 A1 | 2/2012 | Farnikova | |
| 2012/0273354 A1* | 11/2012 | Orhan | A61M 1/284 204/519 |
| 2013/0178834 A1* | 7/2013 | Greenberg | A61M 1/3621 604/522 |
| 2013/0199998 A1* | 8/2013 | Kelly | A61M 1/1696 210/646 |
| 2015/0122712 A1* | 5/2015 | Brandl | A61M 1/16 210/96.2 |
| 2015/0335807 A1* | 11/2015 | Kellum, Jr. | A61M 1/1654 210/632 |
| 2015/0343126 A1* | 12/2015 | Merchant | A61M 1/14 210/660 |
| 2016/0106778 A1* | 4/2016 | hl | A61M 1/3672 210/195.2 |

FOREIGN PATENT DOCUMENTS

| | | |
|---|---|---|
| WO | 2002049693 A2 | 6/2002 |
| WO | WO2003011359 | 2/2003 |
| WO | WO2004056455 | 7/2004 |
| WO | WO2004104160 | 12/2004 |
| WO | WO2005082504 A2 | 9/2005 |
| WO | WO2005113817 | 12/2005 |
| WO | WO2006084276 | 8/2006 |
| WO | WO2006089423 | 8/2006 |
| WO | WO2007146162 | 12/2007 |
| WO | WO2014113740 A1 | 7/2014 |

OTHER PUBLICATIONS

Kaar, Joel L. et al.; Towards Improved Artificial Lungs Through Biocatalysis; Biomaterials; 28; (2007); pp. 3131-3139.
Broun, G. et al.; Facilitated Transport of CO2 Across a Membrane Bearing Carbonic Anhydrase; Febs Letters; vol. 7; No. 3; Apr. 1970; pp. 223-226.
Mancini II, Peter et al.; CO2 Removal for Ventilatory Support: A Comparison of Dialysis With and Without Carbonic Anhydrase to a Hollow Fiber Lung; ASAIO Journal; Trans 3; pp. 675-678.
Salley, S.O. et al.; Immobilized Carbonic Anhydrase in a Membrane Lung for Enhanced CO2 Removal; ASAIO Journal Trans 36;pp. 486-490.
Sally, Steven O. et al.; Thermal, Operational, and Storage Stability of Immobilized Carbonic Anhydrase in Membrane Lungs; ASAIO Journal 1992;38(3); pp. 684-687.
Iwahashi Hidehiko et al. Development of the Oxygenator: Past, Present, and Future; J.Artif. Organs; 2004; 7; pp. 111-120.
Pocker, Y. et al.; The Catalytic Versatility of Erythrocyte Carbonic Anhydrase. IV. Kinetic Studies of the Esterase Activity and Competitive Inhibition by Substrate Analogs; Biochemistry; 1968; vol. 7; No. 9; pp. 3021-3031.
Xu, Haiyan, et al.; Characterizing the Modification of Surface Proteins with Poly(Ethylene Glycol) to Interrupt Platelet Adhesion; Biomaterials; 2006;27; pp. 3125-3135.
Jensen, F.B.; Red Blood Cell pH, the Bohr Effect, and Other Oxygenation Linked Phenomena in Blood O2 and CO2 transport. Acta Physiol Scand; 2004; 182; pp. 215-227.
Cleland, Jeffrey L. et al.; Refolding and Aggregation of Bovine Carbonic Anhydrase B: Quasi-Elastic Light Scattering Analysis; Biochemistry; 1990; 29; pp. 11072-11078.
Stemler, Alan, An Assay for Carbonic Anhydrase Activity and Reactions that Produce Radiolabeled Gases or Small Uncharged Molecules; Anal Biochem; 1993; 210; pp. 328-331.
Lindskog, Sven et al.; The Catalytic Mechanism of Carbonic Anhydrase. Proc Natl Acad Sci USA; 1973; vol. 70; No. 9; pp. 2505-2508.
Smith, Ronald G.; Inorganic Carbon Transport in Biological Systems. Comp Biochem Physiol; 1988; vol. 90B, No. 4; pp. 639-654.
Axen, Rolf et al.; Chemical Fixation of Enzymes to Cyanogen Halide Activated Polysaccharide Carriers; Eur. J. Biochem; 1971; 18; pp. 351-360.
Pariente, F. et al.; Enzyme Support Systems for Biosensor Applications Based on Gold-Coated Nylon Meshes; Biosens Bioelectronlcs; 1996;vol. 11; No. 11; pp. 1115-1128.
Ornovska, Hana, et al.; Surface Properties of Polyethylene After Low-Temperature Plasma Treatment; Colloid Polym Sci; 2003; 281; pp. 1025-1033.
Malpass, Charley A., et al.; Immobilization of an Oxalate-Degrading Enzyme on Silicone Elastomer;J Biomed Mater Res; 2002; 63; pp. 822-829.
Saito, Ryuta, et al.; Structure of Bovine Carbonic Anhydrase II at 1.95 A Resolution; Acta Cryst.; 2004; D60; pp. 792-795.

* cited by examiner

Fig. 6A

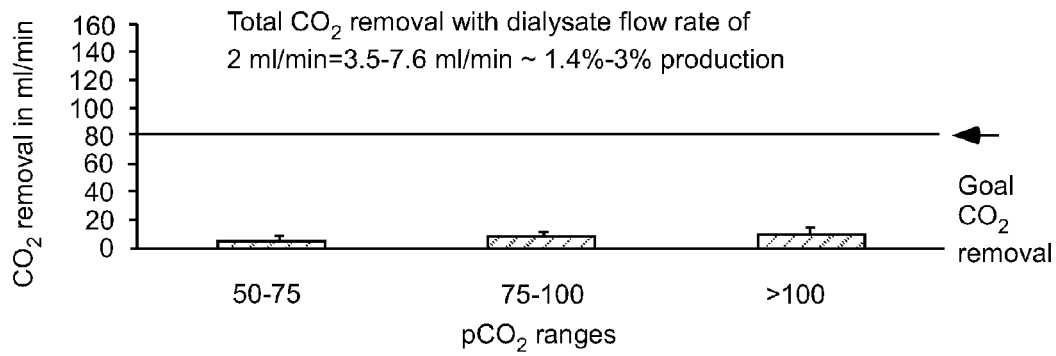

Total $CO_2$ removal with dialysate flow rate of 2 ml/min=3.5-7.6 ml/min ~ 1.4%-3% production

Fig. 6B

TABLE I

| $pCO_2$ ranges | $CO_2$ removal in $CO_2$ (ml/min) | StDev | $CO_2$ removal in Bicarb. (ml/min) | StDev | Total $CO_2$ removal (ml/min) | StDev |
|---|---|---|---|---|---|---|
| 50-75 | 0.14 | 0.02 | 3.4 | 1.5 | 3.54 | 1.52 |
| 75-100 | 0.47 | 0.25 | 5.2 | 1.4 | 5.67 | 3.65 |
| >100 | 0.85 | 0.3 | 6.8 | 4.7 | 7.65 | 5.0 |

Fig. 7A

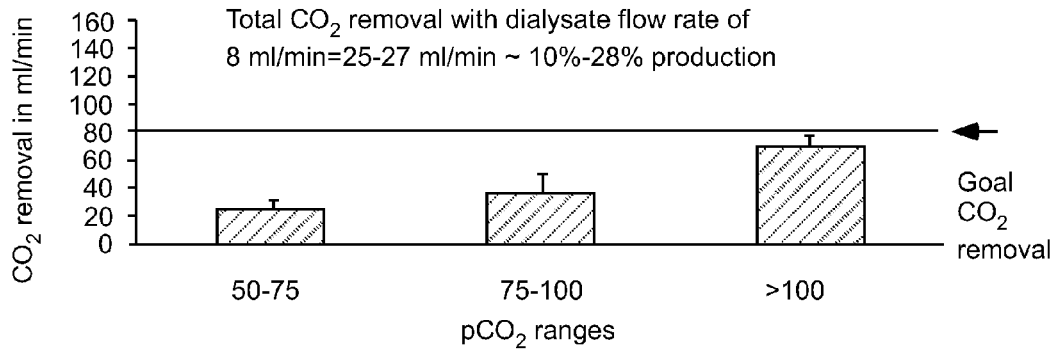

Total $CO_2$ removal with dialysate flow rate of 8 ml/min=25-27 ml/min ~ 10%-28% production

Fig. 7B

TABLE II

| $pCO_2$ ranges | $CO_2$ removal in $CO_2$ (ml/min) | StDev | $CO_2$ removal in Bicarb. (ml/min) | StDev | Total $CO_2$ removal (ml/min) | StDev |
|---|---|---|---|---|---|---|
| 50-75 | 2.9 | 0.5 | 22.5 | 3.1 | 25.4 | 3.6 |
| 75-100 | 3.9 | 0.6 | 31.4 | 13.0 | 35.4 | 13.6 |
| >100 | 7.8 | 2.6 | 62.2 | 3.2 | 70.0 | 5.7 |

Fig. 8A
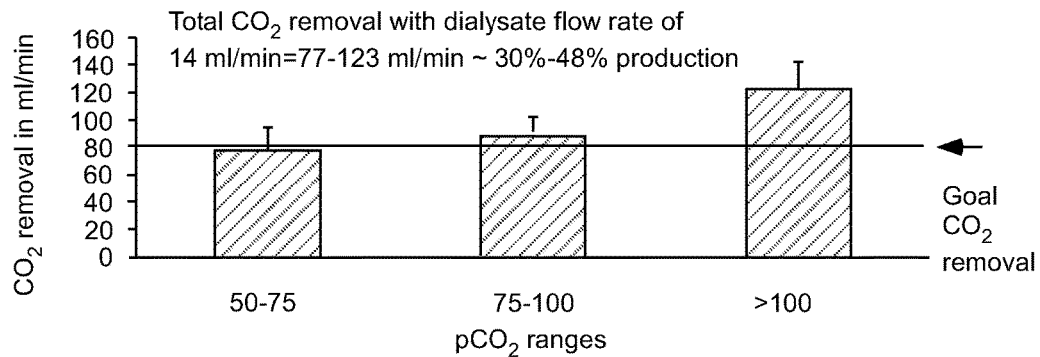
Fig. 8B
TABLE III
| pCO$_2$ ranges | CO$_2$ removal in CO$_2$ (ml/min) | StDev | CO$_2$ removal in Bicarb. (ml/min) | StDev | Total CO$_2$ removal (ml/min) | StDev |
|---|---|---|---|---|---|---|
| 50-75 | 9.4 | 0.9 | 67.9 | 15.6 | 77.3 | 16.5 |
| 75-100 | 10.5 | 1.2 | 78.1 | 13.1 | 86.6 | 16.3 |
| >100 | 15.9 | 0.9 | 107.1 | 18.2 | 123.0 | 19.1 |
Fig. 9A
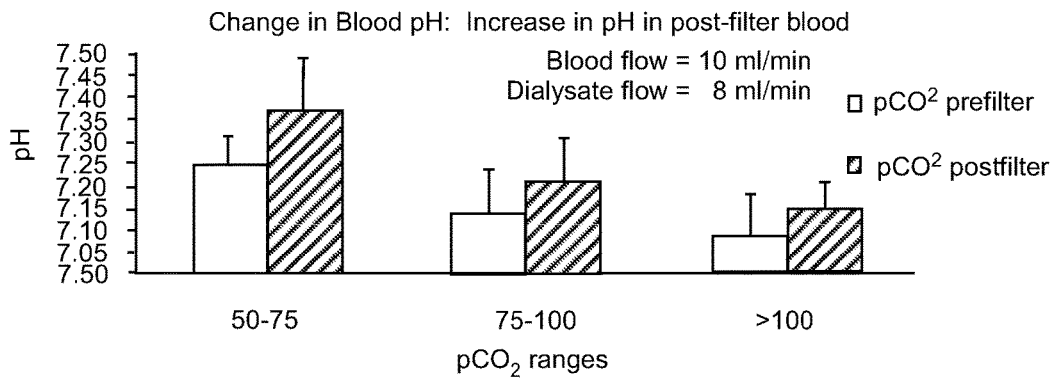
Fig. 9B
TABLE IV
| pH | pCO$_2$ range | | |
|---|---|---|---|
| | 50-75 | 75-100 | >100 |
| pH in | 7.25 | 7.14 | 7.09 |
| pH out | 7.37 | 7.21 | 7.15 |
| StDev in | 0.06 | 0.1 | 0.09 |
| StDev out | 0.12 | 0.1 | 0.06 |

REMOVAL OF CARBON DIOXIDE VIA DIALYSIS

CROSS-REFERENCE TO RELATED APPLICATION

This application is a national phase filing of PCT International Patent Application No. PCT/US2014/012151, filed Jan. 18, 2014, which claims benefit of U.S. Provisional Patent Application Ser. No. 61/754,435, filed Jan. 18, 2013, the disclosures of which are incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

$CO_2$ is an end-product of energy metabolism in all mammals, including humans. Under normal circumstances, it is removed by expiration. $CO_2$ is transported to the lungs by the blood stream, where it exists mostly in the form of bicarbonate ($HCO_3^-$) as a result of the following equilibrium reaction:

$$CO_2 + H_2O <=> H_2CO_3 <=> H^+ + HCO_3^- \qquad (1)$$

High levels of $CO_2$ may be tolerated to some extent, but, if not corrected, lead to progressive mental obtundation, reduced respiratory drive, and resultant alveolar hypoventilation, hypoxemia, acidosis and death. Many critically ill patients, therefore, require mechanical ventilation in the intensive care unit. Mechanical ventilation, although indispensable for survival, may worsen the injured lung and may increase the mortality rate if inappropriately administered. This is particularly true for acute respiratory distress syndrome (ARDS), in which several studies demonstrated that the main reason for high mortality (30-50%) is not severe hypoxemia but rather multi-organ failure (kidneys, heart, liver, etc.), potentially caused by the translocation of various mediators from the lungs through the systemic circulation to peripheral organs and/or augmented by artificial ventilation (ventilator-induced lung injury, VILI). There is good evidence that low volume lung protective ventilation (LPV) improves outcomes in ARDS, but there is also evidence that hypercapnia (high plasma $CO_2$ levels) as a result of reduction of ventilatory volumes prevents the successful application of LPV. Furthermore, recent studies have shown that lung hyperinflation still occurs in approximately 30% of ARDS patients, even though they are being ventilated "correctly" using the National Heart, Lung, and Blood Institute ARDS Network (ADRSNet) strategy. These studies also suggested that some patients may benefit from a further reduction of tidal volume ($V_T$) even when peak plateau pressure (PPLAT) is less than 30 cm $H_2O$.

Extracorporeal carbon dioxide removal (ECCOR) is a technology that has been available for 40 years, and has helped in addressing this problem to an extent. ECCOR involves removal of blood from the patient, which is pumped through an artificial lung (oxygenator membrane) where $CO_2$ is removed and subsequently the purified blood is returned to the patient. However, ECCOR through an artificial lung is under-utilized, largely because it is only available in specialist centers and is complicated to use.

Continuous Renal Replacement Therapy (CRRT), is a widely available and less invasive technology than ECCR. Normally, CRRT (like routine hemodialysis) adds bicarbonate (or buffers such as acetate that are metabolized to bicarbonate) to the blood. Attempts to remove $CO_2$/bicarbonate using CRRT have failed because of the development of metabolic acidosis despite addition of a base (typically, in the form of sodium hydroxide) to the returning blood. Attempts to replace bicarbonate with another anion such as tris(hydroxymethyl)aminomethane (TRIS), acetate, citrate and lactate also failed.

SUMMARY

In one aspect, a method of reducing the concentration of carbon dioxide in blood plasma includes removing blood from a patient and treating (or processing) at least blood plasma of the blood by flowing the blood plasma on one side of at least one semi-permeable membrane and flowing a dialysate on the other side of the at least one semi-permeable membrane. The dialysate has a concentration of bicarbonate less than the concentration of bicarbonate in the blood plasma before treating the blood plasma and has a composition such that the blood plasma strong ion difference that results from treating the blood plasma in conjunction with an achieved reduction in blood plasma $CO_2$ concentration results in a blood plasma pH that does not result in metabolic acidosis. For example, the reduction in blood plasma $CO_2$ concentration may result in a blood plasma pH that does not change by more than +/−0.5 during treatment. The blood pH after treatment may, for example, be in the range of 7.30 to 7.45. The method may also include returning the blood plasma to the patient after treating the blood plasma on one side of the at least one semi-permeable membrane. In a number of embodiments, the concentration of bicarbonate in the dialysate is no more than half the concentration of bicarbonate in the blood plasma before treating the plasma. In a number of embodiments, the concentration of bicarbonate is in the range of 5 mmol to 0 mmol. In a number of embodiments, the concentration of bicarbonate in the dialysate is zero. The treating or processing of the blood plasma may, for example, also provide renal replacement therapy.

In general, blood plasma is the liquid portion of human blood or whole blood. The blood plasma may be separated from blood (as, for example, in plasma exchange). In a number of embodiments hereof, the blood (including the blood plasma) flows on one side of at least one semi-permeable membrane and the blood (including the blood plasma) is returned the patient. In other words, whole blood is treated and returned to the patient. However, in other embodiments, blood plasma may be separated from the blood and caused to flow on the one side of the at least one semi-permeable membrane. Unless the context clearly dictates otherwise, when blood plasma is referenced herein, it may be as a component of blood (whole blood) or as blood plasma separated from blood. In general, semi-permeable membrane is a thin layer of material (which may, for example, include holes of various sizes, or pores). Under the conditions of operation, smaller solutes and fluid pass through the membrane, but the membrane blocks the passage of larger substances (for example, red blood cells, large proteins, etc.). In general, ions may pass or diffuse through the semi-permeable membranes with little resistance.

The method may, for example, further include, reducing the concentration of carbon dioxide in the dialysate after the dialysate contacts at least one semi-permeable membrane and recycling the dialysate after reducing the concentration of carbon dioxide.

In a number of embodiments, carbonic anhydrase is immobilized on or in the vicinity of the at least one semi-permeable membrane.

The method may, for example, further include increasing the pH of the blood plasma before the blood plasma flows on one side of the at least one semi-permeable membrane and decreasing the pH of the blood plasma after the blood plasma flows on one side of the at least one semi-permeable membrane.

The composition of the dialysate may, for example, be determined on a per-patient basis or standardized for multi-patient use. In a number of embodiments, the composition of the dialysate is determined (at least in part) on the basis of at least one of a level of hypercarbia, a level of respiratory acidosis and a level of metabolic acidosis. The composition of the dialysate may, for example, be determined (at least in part) on the basis of at least one of a patient baseline blood plasma $CO_2$ concentration, a desired blood plasma $CO_2$ concentration, blood plasma strong ion difference and blood plasma weak acid concentration.

In another aspect, a system for reducing concentration of carbon dioxide in blood plasma includes a dialysis filter system comprising at least one semi-permeable membrane, and a source of a dialysate having a concentration of bicarbonate less than the concentration of bicarbonate in the blood plasma before treating the blood plasma and having a composition such that the blood plasma strong ion difference that results from treating the blood plasma, in conjunction with an achieved reduction in blood plasma $CO_2$ concentration, results in a post-treatment blood plasma pH as described above (for example, that does not change by more than +/−0.5 during treatment).

In a further aspect, a dialysate for use with blood plasma has a concentration of bicarbonate less than a baseline concentration of bicarbonate in the blood plasma and has a composition such that the blood plasma strong ion difference that results from treating the blood plasma with the dialysate in a dialysis procedure, in conjunction with an achieved reduction in blood plasma $CO_2$ concentration, results in a post-treatment blood plasma pH as described above (for example, that does not change by more than +/−0.5 during treatment).

In still a further aspect, a method of formulating a dialysate includes providing a concentration of bicarbonate less than a baseline concentration of bicarbonate in blood plasma and providing a composition such that the blood plasma strong ion difference that results from treating the blood plasma with the dialysate in a dialysis procedure, in conjunction with an achieved reduction in blood plasma $CO_2$ concentration, results in a post-treatment blood plasma pH as described above (for example, that does not change by more than +/−0.5 during treatment). The dialysate may, for example, include a solution having a concentration of bicarbonate less than the half the concentration of bicarbonate in blood plasma.

The present devices, systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 6A illustrates removal of $CO_2$ with a dialysate including no bicarbonate at a dialysis flow rate of 2 ml/min for various plasma $pCO_2$ ranges.

FIG. 6B illustrates Table I, which sets forth data for the graph of FIG. 6A.

FIG. 7A illustrates removal of $CO_2$ with a dialysate including no bicarbonate at a dialysis flow rate of 10 ml/min for various plasma $pCO_2$ ranges.

FIG. 7B illustrates Table II, which sets forth data for the graph of FIG. 7A.

FIG. 8A illustrates removal of $CO_2$ with a dialysate including no bicarbonate at a dialysis flow rate of 14 ml/min for various plasma $pCO_2$ ranges.

FIG. 8B illustrates Table III, which sets forth data for the graph of FIG. 8A.

FIG. 9A illustrates change in blood pH with a dialysate including no bicarbonate at a dialysis flow rate of 10 ml/min for various plasma $pCO_2$ ranges.

FIG. 9B illustrates Table IV, which sets forth data for the graph of FIG. 9A.

DETAILED DESCRIPTION

Figure 1:
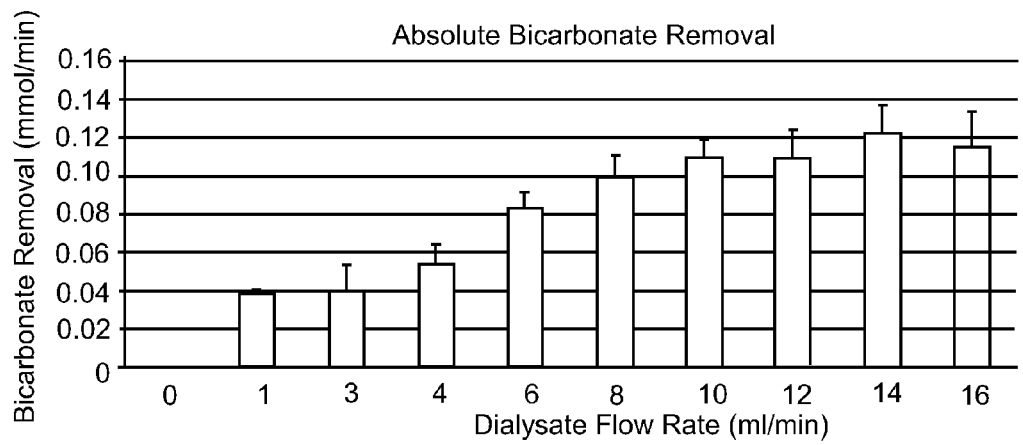
FIG. 1 illustrates the results of bicarbonate removal (mmol/min) using an in vitro test system at various dialysate flow rates (ml/min).

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a membrane" includes a plurality of such membranes and equivalents thereof known to those skilled in the art, and so forth, and reference to "the membrane" is a reference to one or more such membranes and equivalents thereof known to those skilled in the art, and so forth.

In a number of representative embodiments, devices, systems, compositions and/or methods hereof provide minimally invasive strategies to remove carbon dioxide ($CO_2$) in the form of bicarbonate using continuous renal replacement therapy (CRRT). CRRT is a more widely available and less invasive technology that ECCOR to remove $CO_2$. As described above, $CO_2$ is predominantly transported in the blood not as $CO_2$ gas or dissolved $CO_2$ but as bicarbonate ion ($HCO_3^-$).

Dialysates used in CRRT circuits include added bicarbonate to the blood to treat metabolic acidosis from renal failure. In that regard, bicarbonate levels used in dialysis solutions are set slightly higher than normal blood levels to encourage diffusion of bicarbonate into the blood and to act as a pH buffer to neutralize the metabolic acidosis that is often present in these patients. However, in a number of embodiments hereof, low bicarbonate dialysate solutions (that is, dialysate solutions having a bicarbonate concentration less than that present in blood) are used create a driving force in the form of a concentration gradient to increase the diffusion of bicarbonate from the blood. $CO_2$ is thereby removed, reducing the ill-effects of progressive hypercapnia and resultant inability to use LPV. Previously, attempts to remove bicarbonate/$CO_2$ via CRRT have been found to be difficult because of development of metabolic acidosis with bicarbonate removal. The use of CRRT for $CO_2$ removal has thus not been successful despite addition of a base in the form of sodium hydroxide to the returning blood.

In a number of embodiments hereof, dialysate compositions containing low levels of bicarbonate (including substantially no or no bicarbonate) are used to maximize $CO_2$ removal in the form of bicarbonate by diffusion while preventing acidosis. Such dialysate compositions may, for example, be tailored to individual patients. In a number of embodiments, the strong ion difference model is used in formulating stable dialysate compositions hereof. The dissolved bicarbonate anion readily passes across dialysis membranes. Developing a dialysis system to remove bicarbonate shifts the equilibrium of equation (1), reducing $CO_2$ levels as bicarbonate is removed. Using a dialysis system to maximize bicarbonate removal has the potential to make extracorporeal $CO_2$ removal available to any facility that is capable of providing dialysis, and would be no more invasive that standard dialysis.

Acid-base chemistry demonstrates that the bicarbonate present in plasma is dictated by the $CO_2$ level and the strong ion difference as well as blood weak acid concentration. The weak acid concentration will not be altered in a number of embodiments hereof. In a number of embodiments, the dialysate compositions hereof are designed to control the strong ion difference rather than replacing bicarbonate (with another anion) in the plasma. The strong ion difference or SID is defined as the difference between the sum of concentrations of strong cations and strong anions as follows:

$$SID = \Sigma[\text{strong cation charge concentration}] - \Sigma[\text{strong anion charge concentration}] \quad (2)$$

Strong ions are those that dissociate totally at the pH of interest (for example, physiological pH). For example, SID may be given by:

$$[SID] = [Na^+] + [K^+] + [Ca^{2+}] + [MG^{2+}] - [CL^-] - [\text{Other Strong Anions}] \quad (3)$$

Acid-base balances employing strong ionic difference as a means of assessing clinical acid-base disturbances were set forth by Stewart. Stewart, P. A., *How to understand acid-base. A quantitative acid-base primer for biology and medicine*, New York/Oxford: Elsevier (1981) and Stewart, P. A., Modern quantitative acid-base chemistry, *Can J Physiol Pharmacol*, 61:1444-1461 (1983), the disclosures of which are incorporated herein by reference. Stewart's acid-base theory is, for example, discussed in Corey, H. E., "Stewart's acid-base theory: Equation, implementation and mechanism," *Trends in Comparative Bichem. & Physiol.*, 14:35-54 (2009), and Ring, T, "Mixing bicarbonates: dilution acidosis from first principles," Intensive Care Med., December; 35(12):2183-4 (2009), the disclosures of which are incorporate herein by reference.

In general, there are three variables which are amenable to change in-vivo: partial pressure of carbon dioxide ($PCO_2$), total weak non-volatile acids [$A_{TOT}$], and net Strong Ion Difference [SID]. The influence of these three variables can be predicted through six simultaneous equations (see, for example, Appendix A):

$[H^+] \times [OH^-] = K_w$ (water dissociation equilibrium)

$[H^+] \times [A^-] = K_a \times [HA]$ (weak acid)

$[HA] + [A^-] = [A_{TOT}]$ (conservation of mass for "A")

$[H^+] \times [HCO_3^-] = K_1' \times PCO_2$ (bicarbonate ion formation equilibrium)

$[H^+] \times [CO_3^{2-}] = K_3 \times [HCO_3^-]$ (carbonate ion formation equilibrium)

$[SID] + [H^+] - [HCO_3^-] - [A^-] - [CO_3^{2-}] - [OH^-] = 0$ (electrical neutrality)

The dialysate hereof contain a low bicarbonate concentration, but exhibit a pH that is tolerated by blood (that is, does not harm blood cells) passing through a dialysis filter including at least one semi-permeable membrane as known in the dialysis arts. The dialysate is designed to maintain plasma pH and prevent acidosis developing after the removal of bicarbonate. This result is achieved by composing the dialysate so as to achieve a plasma strong ion difference that will achieve a normal blood pH at the desired level of $PCO_2$. Previous attempts to use dialysis to remove bicarbonate have been abandoned as a result of the development of metabolic acidosis and an inability to find a suitable replacement buffer for bicarbonate. The bicarbonate present in plasma is dictated by the $CO_2$ level and the strong ion difference. Therefore, the dialysates hereof are designed to control the plasma strong ion difference in relation to the target blood $PCO_2$ rather than replacing bicarbonate with an alternative buffer.

In a number of embodiments hereof, a mathematical model was developed based on an advanced understanding of acid-base physiology to precisely control pH by targeting changes in plasma strong ion difference (SID) instead of bicarbonate itself. The bicarbonate flux is controlled through the choice/design of the hemofilter and the dialysate.

In formulating a dialysate for use herein, the SID of the plasma was set by solving the Stewart equation for the desired $CO_2$ and pH as follows:

$$SID + [H^+] - \frac{K_c * pCO_2}{[H^+]} - \qquad (4)$$

$$2 * \frac{K_c * K_3 * pCO_2}{[H^+]^2} - \frac{K_w}{[H^+]} - \frac{K_A * [A_{tot}]}{K_A + [H^+]} = 0$$

wherein,
$K_w = 2.39 \times 10^{-14}$ mol$^2$/L$^2$;
$K_e = 2.45 \times 10^{-11}$ mol$^2$/L$^2$ mm Hg;
$K_3 = K_2(H_2CO_3) = 5.76 \times 10^{-11}$ mol/L; and
$K_a = 1.77 \times 10^{-7}$ mol/L.

Usually, the sieving coefficient of small molecules is considered to be 1 across the dialysis filter and a 1:1 mixing is often assumed. The sieving coefficient provides a measure of equilibration between the concentrations of two mass transfer streams. The sieving coefficient is defined as the ratio of solute filtrate concentration ($C_f$) to the respective solute plasma concentration ($C_p$) or $C_f/C_p$. A sieving coefficient of 1 indicates unrestricted transport. However, the mixing may not always be 1:1 and it may depend on the change in the sieving coefficient as seen in bench and clinical experiments of continuous dialysis with diffusion and convection as mechanisms. In a number of embodiments, modifications were made to the Stewart equation to factor this change and create a mixing equation including the sieving coefficient for calculation of the SID of a mixed solution as follow:

$$SID = \{K_c*pCO_2/[H^+] - 2*K_cK_3*pCO_2/[H^+]^2 - K_w/[H^+] \\ K_a*[A_{tot}]/(K_a+[H^+]) - [H^+]\}*(1-\sigma) \qquad (5)$$

In the above equation, σ is a reflection coefficient of the molecules in the plasma, and (1−σ) is the sieving coefficient. In ideal circumstances, this is zero. In general, the relevant ions may pass or diffuse through the semi-permeable membranes with little resistance. The inventors determined the target $CO_2$, held pH constant, and solved for the new SID. We then calculated the composition of a dialysate that would be required to achieve the new SID. The expected SID with a $CO_2$ level of 50 mmHg is around 29 mmol Based on this, the following were added to 1 L of deionized water: 10 mmol of NaOH=400 mg; 112.5 mmol of NaCl=6.63 g; 3.5 mmol of KCl=261 mg; 1 mmol of MgCl=60 mg; 3 mmol of lactate=366 mg (or 50% solution in water added 0.54 ml); 11 mmol NaHCO$_3$=924 mg; and 0.5 mmol NaH$_2$PO$_4$=60 mg. The solution was titrated with HCl to achieve a pH of approximately 8.0. For example, 1 ml of HCl (6N) was added to change from pH 10.1 to pH 8.14. This dialysate mixture was tested, including its ability to maintain pH while removing $CO_2$ from the plasma (see, for example, FIGS. 1 through 4). We also calculated the SID of the dialysate in the steady state which, when compared to the expected SID by the equation above, will help to calculate a correction factor for reflection and sieving coefficient. The dialysate mixture may be tested at different levels of $CO_2$ to assess the efficiency of $CO_2$ removal.

Removing sufficient bicarbonate may, for example, require a higher flow rate than used in normal dialysis. Strategies that may, for example, be employed to manage flow requirements include, but are not limited to: (a) increasing the surface area of the dialysis filter and (b) a strategy for recycling the dialysate, including removing the bicarbonate therein. Removal of bicarbonate from dialysate may, for example, be achieved using aeration or modified gas exchange membranes. Other strategies include, for example, forcing precipitation of the bicarbonate or developing an anion exchange membrane or using hemadsorption technology. Recycling dialysate is attractive. For example, it will prevent loss of essential minerals and amino acids, but will still allow concomitant renal replacement therapy by using hemofiltration. Another strategy may, for example, include altering the plasma with alkalinizing agents or electrochemically and removing these chemicals after the filter before returning the blood to the patient using hemofiltration, hemodialysis or hemoadsorption.

Figure 2:
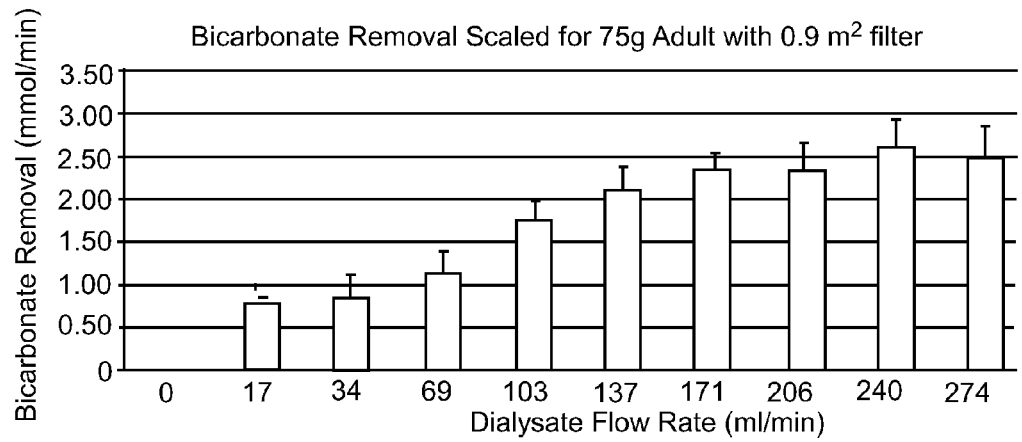
FIG. 2 illustrates the data of FIG. 1 scaled up to a 0.9 m$^2$ dialysis filter (as commonly used to provide CRRT in intensive care in connection with a 75 kg man).
Figure 3:
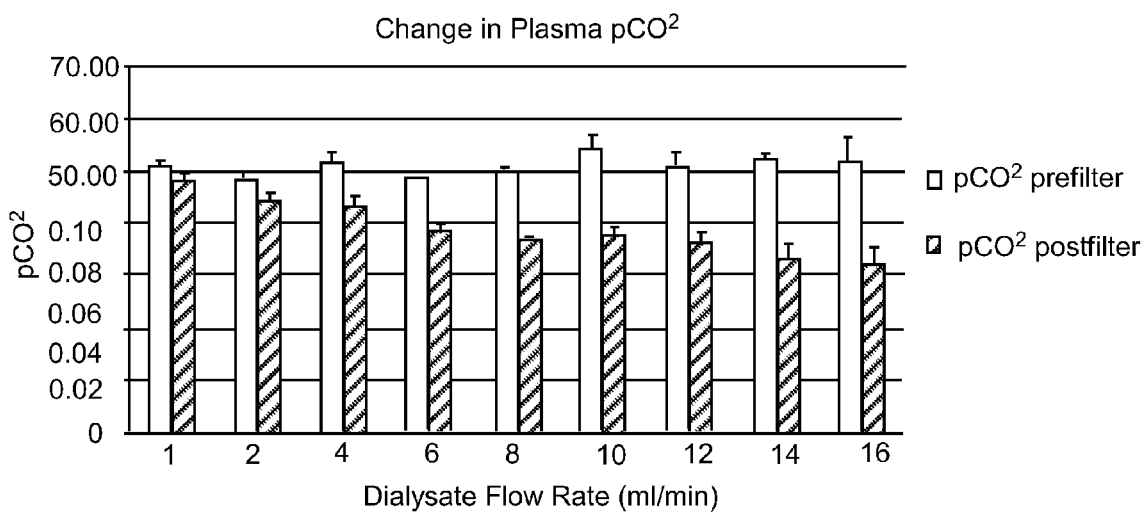
FIG. 3 illustrates the lowering of the $pCO_2$ of the plasma solution in vitro post-filter at various dialysate flow rates.

The representative studies of FIGS. 1 through 4 illustrate in vitro bench data that demonstrate successful removal of $CO_2$ from a plasma-like solution using a dialysate with a low bicarbonate concentration and a physiologic sodium concentration as described above. The chloride concentration of the dialysate was slightly supra-physiologic (118 mmol/L), but it is well within tolerance limits for human use. FIG. 1 illustrates the level of bicarbonate removal using the in vitro system of FIG. 5 at various dialysate flow rates. FIG. 2 illustrates the data of FIG. 1 scaled up to a 0.9 m$^2$ dialysis filter in a 75 kg man. FIG. 3 illustrates the lowering of the pCO$_2$ of the plasma solution in vitro as measured before the dialysate filter and after the dialysate filter at various dialysate flow rates.

Figure 4:
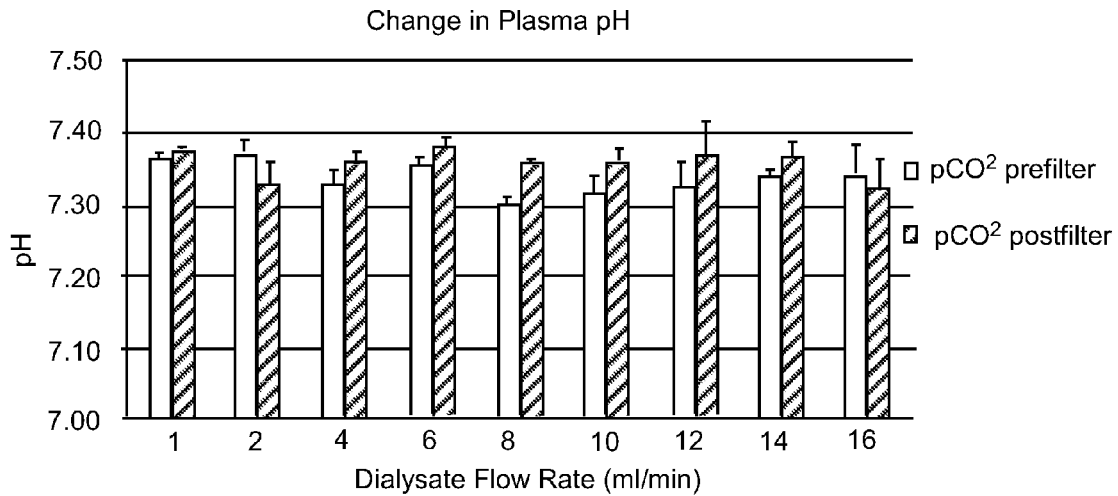
FIG. 4 illustrates the maintenance of pH of the plasma solution by maintaining the strong ion difference pre- and post-filter.

The experimental data show that a dialysate hereof with a bicarbonate concentration of 10 mmol/L removes equivalent of 2-2.5 mmol/min of bicarbonate. Bicarbonate levels in a healthy adult may, for example, be in the range of 22-29 mmol/L. In these studies, dialysate flow rates of approximately 7 times higher than standard continuous dialysis flow rates were used for maximal removal and more equivalent to flows used in standard intermittent hemodialysis. As illustrated in FIG. 4, post-filter pH is maintained, and is slightly higher at certain flow rates, thereby, eliminating metabolic acidosis which had hampered previous attempts at using CRRT for $CO_2$ removal.

Figure 5:
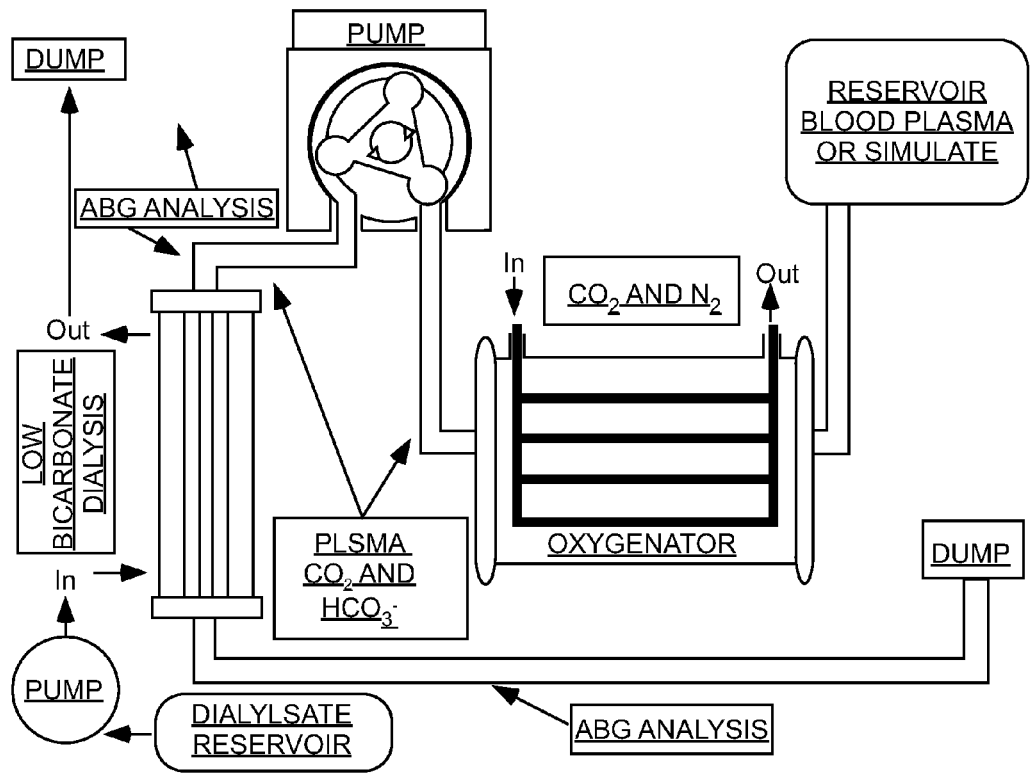
FIG. 5 illustrates a representative embodiment of an in vitro system or circuit hereof used for $CO_2$ removal in the form of bicarbonate.

As illustrated in FIG. 5, in the studies hereof, a simulated blood plasma (described in further detail in the Experimental Example section), was delivered from a reservoir and passed through an "oxygenator" device or system. In normal operation, an oxygenator device or system serves as a lung assist device or system, and is designed to expose the blood to oxygen and remove carbon dioxide. The oxygenators includes hollow fiber membranes permeable to gas but impermeable to blood. The blood flows on the outside of the hollow fibers, while oxygen flows in the opposite direction on the inside of the fibers. As the blood passes through the oxygenator, the blood comes into intimate contact with the hollow fiber membranes. Gas containing oxygen is delivered to the interface between the blood and the device. Carbon dioxide passes from the blood and into the hollow fiber membranes for removal.

In the present system, however, a mixture of carbon dioxide and nitrogen was passed through the hollow fiber membrane to introduce carbon dioxide into the simulated blood plasma. The system was operated to result in a generally consistent 50 mmHg $CO_2$ partial pressure.

The plasma (containing carbon dioxide) leaving the oxygenator is pumped to the dialysis filter. The $CO_2$ concentration and $CO_2$ partial pressure were measured before the plasma entered the dialysis filter and after the plasma exited the dialysis filter. In the dialysis filter, the plasma flows through semi-permeable fibers and the dialysate flows around the fibers. After passing through the dialysis filter, the plasma flowed to a plasma dump and the dialysate flowed to a dialysate dump.

Dialysate composition may, for example, be altered or optimized on a per-patient basis. For example, a model based on the physico-chemistry of different levels of hypercarbia and respiratory with/without metabolic acidosis may be used to create a tailored-to-patient dialysis solution based on the patients acid-base status and the desired change in $CO_2$. For example a given patient may have any combination of baseline $CO_2$, desired $CO_2$, plasma strong ion difference and plasma weak acid concentration. Furthermore, a patient may have combined lung and kidney failure and the dialysate composition may be customized so that it may, for example, serve the dual purposes of ECCOR and CRRT. Thus, in a number of embodiments, a method is provided for tailored fluid composition. A "standard" fluid composition may be used in an "average" case, and a technique to use CRRT with the fluid at specific flow rates to achieve sufficient control of $CO_2$.

Figure 10:
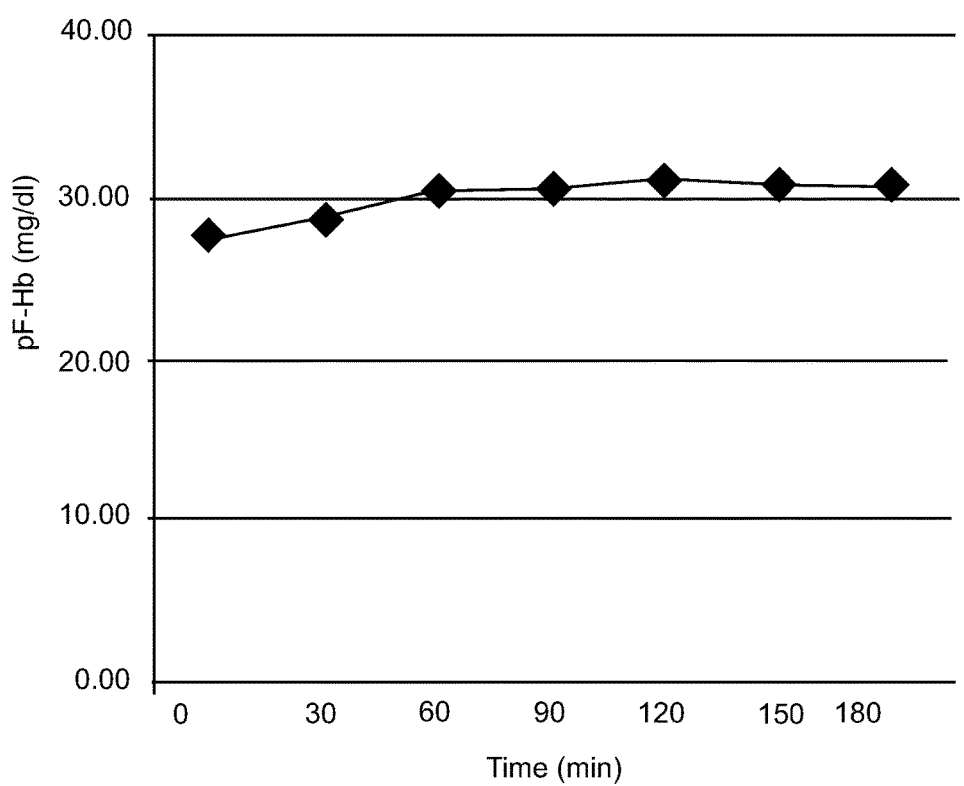
FIG. 10 illustrates a graph of measured plasma-free hemoglobin levels over time in a recirculating loop model, showing no hemolysis.

Moreover, as clear to one skilled in the art, reducing the concentration of bicarbonate in the dialysate can be decreased to increase the concentration across the dialysate membrane and increase the rate of bicarbonate removal from the plasma. In several studies, a dialysate having a zero concentration of bicarbonate therein was used. In such studies, bovine blood was drawn one day prior to the procedure and refrigerated was used. Normal acid-base and blood gas parameters were assessed. $CO_2$ was added to the plasma as set forth in FIG. 5 using a MINIMAX® plus hollow fiber oxygenator (available form Medtronic, of Anaheim, Calif. USA) with a sweep gas composed of $N_2$ and $CO_2$. The ratio of the $N_2$ and $CO_2$ in the sweep gas was set to ensure a $CO_2$ partial pressure ($pCO_2$) between 60-100 mmHg for the blood exiting the oxygenator. The solution was then pumped through an M10 dialysis filter (available from Gambro of Lyon, France; surface area 0.04 $m^2$). The dialysate was created using common chemical constituents as described above. However, the dialysate included no bicarbonate. Flow rates were scaled down from conventional dialysis based on filter surface area. The plasma flow rate was set at 10 mls per minute, which is the equivalent of 200 mls per minute for a full-sized filter. Such flows are readily achievable with current available continuous veovenous hemodialysis (CVVHD) devices. Pre- and post-filter acid-base analysis was assessed using a blood gas analyzer. Similar to the studies above, the dialysate was successful in removing $CO_2$ in the form of bicarbonate and also preserved plasma pH. A representative goal of 30% $CO_2$ removal was set forth in the studied of FIGS. 6A through 8B. As, for example, illustrated in FIGS. 6A through 8B, in vitro studies showed that almost 50% of $CO_2$ production can be removed, depending upon dialysate flow rate. Dose-response saturation of $CO_2$ removal occurred at around 240 ml/kg/hr; this is eight time typical CVVHD flow (25-30 ml/kg/hr), but similar to Intermittent Hemodialysis (IHD) flows. As set forth above, recycling the dialysate can address the loss of essential minerals and increased resource (water) utilization associates with high dialysate flows. As expected, the increased diffusion gradient between the blood and the dialysate with zero bicarbonate resulted in a higher flux of bicarbonate (and therefore $CO_2$). As, for example, illustrated in FIGS. 9A and 9B, post-filter pH was maintained, thereby eliminating concerns of metabolic acidosis. As set forth above, the flow rates in the studies of FIGS. 6A through 9B were scaled down on the basis of the filter surface area. As illustrated in FIG. 10, no hemolysis was noted using the zero-bicarbonate dialysate. Hemolysis was tested by measuring plasma-free hemoglobin levels over time in a recirculating loop model.

Bicarbonate removed from the blood does not need to be replaced, provided the dialysate is formulated to maintain the concentration of strong ions in the plasma, because plasma bicarbonate concentration depends on the concentration of strong ions and the amount of dissolved $CO_2$. Once again, strong ions are derived from salts that completely dissociate when in solution. The most important strong ions in plasma are sodium and chloride.

The devices, systems, methods and compositions hereof may, for example, be used with ARDS patients who would benefit with LPV and $CO_2$ removal as a result of hypercarbia from low ventilatory volumes and for hypercapneic respiratory failure in patients with COPD and/or Acute Cardiogenic/Non-cardiogenic pulmonary edema.

Figure 11:
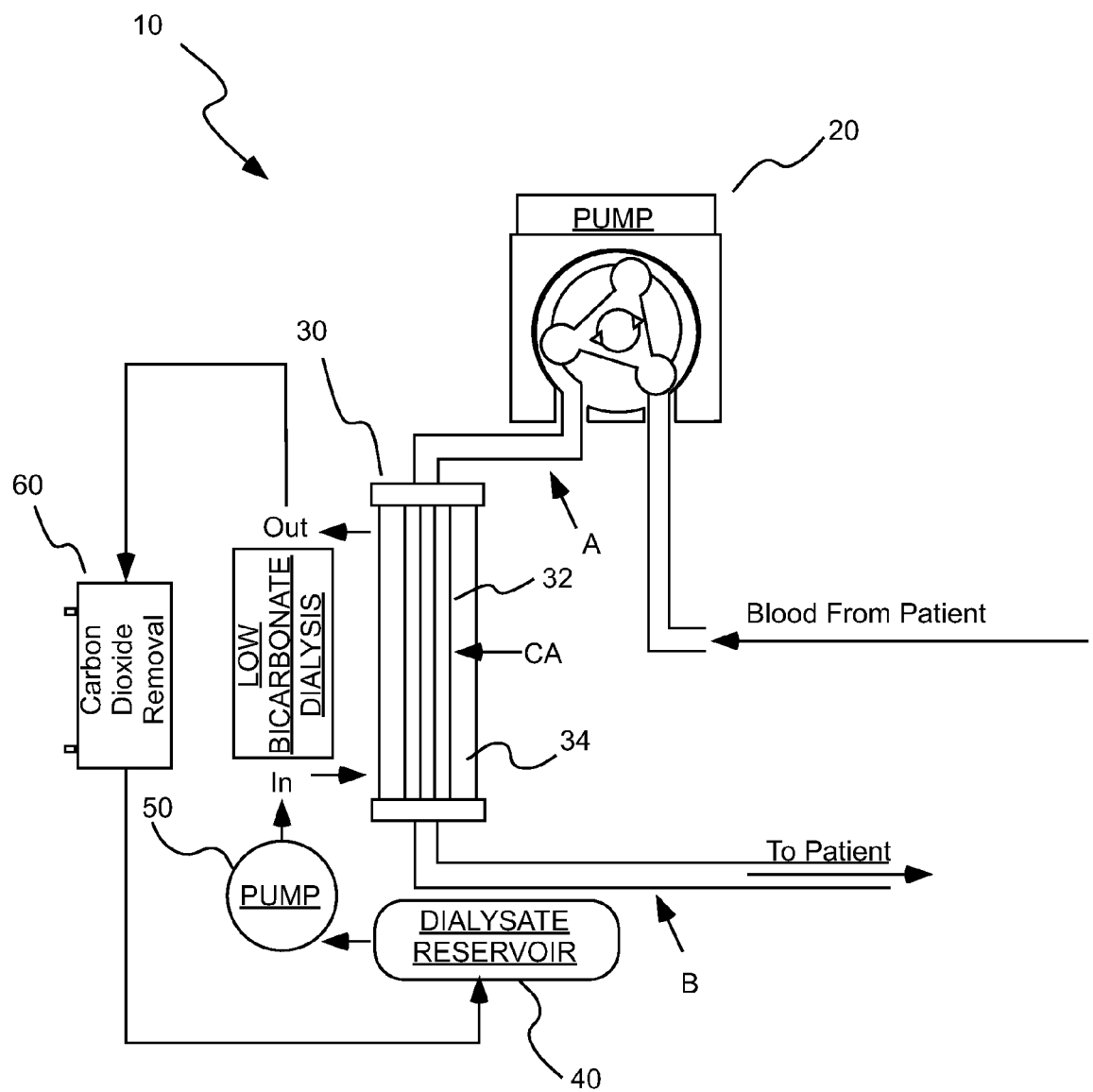
FIG. 11 illustrates a representative embodiment of a system hereof for removal of $CO_2$ from blood/blood plasma.

FIG. 11 illustrates a representative example of a system 10 for reducing the concentration of $CO_2$ in blood plasma. In a number of respects, system 10 is similar to systems currently used in CRRT. In that regard, system 10 includes patient interfaces for removal of blood from the patient and return of filtered blood to the patient. One or more blood pumps 20 as known in the art may be used for pressurization as required. As described above in connection with FIG. 5, a dialyzer or dialysis filter system 30 may, for example, include a plurality of, semipermeable fibers 32. In dialysis filter system 30, the blood flows through semi-permeable fibers 32 and the dialysate flows in a volume 34 around fibers 34. After passing through dialysis filter system 30, the filtered blood is returned to the patient.

In a manner similar to that described in connection with oxygenators or lung assist systems in U.S. Pat. Nos. 7,763,097 and 8,043,411, the disclosure of which are incorporated herein by reference, carbonic anhydrase or CA may be used on or in the vicinity of fibers 32 to drive or increase the removal of bicarbonate from blood. CA reversibly catalyzes hydration of $CO_2$ into carbonic acid, which then rapidly dissociates into bicarbonate ion. Immobilized CA may, for example, be used to facilitate diffusion toward a membrane including the immobilized enzyme. CA immobilized on or in the vicinity of the surface of fibers 32 enables "facilitated diffusion" of $CO_2$ as bicarbonate towards the fibers 32 and enhances the removal rate of $CO_2$.

In a number of embodiments, the blood may be treated before entering dialysis filter system 30 to facilitate $CO_2$ removal and, if necessary, treated after leaving dialysis filter system 30 to, for example, restore one or more properties thereof. For example, to further facilitate removal of $CO_2$ (by forcing more $CO_2$ to be converted to bicarbonate), the blood may be alkalinized (represented by arrow A) before entering dialysis filter system 30 via the addition of, for example, sodium without addition of bicarbonate. For example, sodium hydroxide (NaOH) may be added. After exiting dialysis filter system 30, pH may be restored (decreased) using, for example dilute hydrochloric acid (HCl), In the embodiment of FIG. 6, dialysate is pumped from a reservoir 40 via a pump 50 to flow through volume 34 (around fibers 32). As described above, $CO_2$/bicarbonate may be removed from the dialysate via a $CO_2$ removal system 60. For example, a $CO_2$ removal system as described in U.S. Pat. Nos. 7,763,097 and 8,043,411 may be used. After $CO_2$ removal, the dialysate is recycled to reservoir 40. Recycling may, for example, limit total fluid use while maintaining $CO_2$ clearance, while minimizing loss of essential minerals and micronutrients.

In summarizing embodiments of the methodology set forth above, one may begin by defining a desired or goal (post-treatment) plasma $pCO_2$. Typically, 50 mmol is chosen, which is above the normal range, but is typically significantly less than the patient beginning (pretreatment) plasma $pCO_2$. The desired or goal $pCO_2$ may, for example, change depending upon patient condition. Equation 4 is then used to determine desired plasma SID, assuming $A_{tot}$ remains unchanged and setting $pCO_2$ to the desired level. Equation 4 may, for example, be solved for a desirable pH level. In general, it is desirable that the blood plasma pH does not change by more than +/−0.5 during treatment. In a number of embodiments, a desirable level of blood pH was set in the range of approximately 7.30 to 7.45 of 7.3 to 7.35. The dialysate is formulated so that the dialysate SID is equal to or approximately equal to the desired or determined plasma SID. The dialysate bicarbonate level may then be set to a predetermined level or concentration. For example, the dialysate bicarbonate can be set to 5 mmol or less. In a number of embodiments, the dialysate concentration is set to zero. One may then determine the pH at the membrane/blood plasma interface by solving Equation 5 for mixing of equal amounts of the dialysate and blood plasma. The interfacial pH should be determined to be a biocompatible pH (that is, a pH that will not cause any significant harm to blood/plasma constituents such as red blood cells). In a number of embodiments, a range of desired interfacial pH was set to between approximately 6.5 and 8.5. If the interfacial pH is determined to be outside of the predetermined range one may, for example, add a buffer. Typically a buffer other than bicarbonate is added (for example, HCl or NaOH). If bicarbonate is added, the bicarbonate level is maintained no greater than ½ the beginning plasma level, no greater than 10 mmol or, in most cases, no greater than 5 mmol. As set forth above, minimizing the level of bicarbonate in the dialysate increases the driving force for diffusion of bicarbonate across the membrane, and thus facilitates removal of bicarbonate/$CO_2$ from the blood/plasma.

The dialysates and systems of the present studies were not optimized. Dialysate composition may, for example, be mathematically modeled based on a physicochemical approach to acid-base physiology. Data from experiments and literature studies may, for example, be used to mathematically model $CO_2$ removal by dialysis as described herein. Semi-permeable membranes used in the dialysis filter systems may, for example, be modified to enhance bicarbonate flux. For example, as described above, carbonic anhydrase, may be immobilized in the vicinity of the membrane surface. Further, different types of dialysis recycling processes may be used to effect $CO_2$ removal (for example, sorbent adsorption, ion trapping, photobio-filter using biological agents etc.).

Experimental

Preparation of Phosphate Buffered Saline (PBS) Simulated Blood Solution

Beginning with 780 ml of PBS, deionized water was added to increase the volume a to 1 L with deionized $H_2O$, to which 30 mmol of $NaHCO_3$ (2.52 g) was added. Also added were Na 143 mmol/l, K 4 mmol/l, Cl 110 mmol/l, and $PO_4$ 4 mg/dl. During studies, $CO_2$ was added to partial pressure 50 mmHg (via a 70/30 $N_2/CO_2$ mix) using an "oxygenator" as illustrated in FIG. 5. As described above, such devices are typically used for the removal of carbon dioxide and the oxygenation of blood. See, for example, U.S. Pat. Nos. 7,763,097 and 8,043,411. In the present studies, $CO_2$ was added to the simulated blood solution by passing the mixture of 70/30 $N_2/CO_2$ through fibers around which the simulated blood solution passed (see FIG. 5).

Dialysate Preparation.

The following were added to 1 L of deionized water: 10 mmol of NaOH=400 mg; 112.5 mmol of NaCl=6.63 g; 3.5 mmol of KCl=261 mg; 1 mmol of $MgCl$=60 mg; 3 mmol of lactate=366 mg (or 50% solution in water added 0.54 ml); 11 mmol $NaHCO_3$=924 mg; and 0.5 mmol $NaH_2PO_4$=60 mg. The solution was titrated with HCl to achieve a pH of approximately 8.0. For example, 1 ml of HCl (6N) was added to change from pH 10.1 to pH 8.14.

Studies.

During studies hereof a system including flow circuits and pumps was set up as set forth in FIG. 5. The simulated blood solution was passed through the dialysis filter at 18.67 (18.7) ml/min, while the dialysate was passed through at 1.5 through to 18.7 ml/min. The "oxygenator" was operated to result in a consistent 50 mmHg $CO_2$ partial pressure. The "blood" gas compositions ($CO_2$ concentration) into the dialysis filter system and out of the dialysis filter system were measured at steady states.

Post-Study Care.

After the study procedure, the oxygenator was flushed with DI water over night (if only PBS simulated blood solution was used). Subsequently, both the fluid side and gas side of the hollow fiber membranes (HFMs) were dried overnight with nitrogen or air from, for example, a central line (equipped with an air filter). If blood was used in the studied, the loop was flushed with PBS to wash away most of the red blood cells (RBC's). After flushing with PBS, the system was rinsed with deionized water. Subsequently, a 2-3 day wash with TERGAZYME® (enzyme-active powdered detergent available from Alconox of White Plains, N.Y.) to clean the oxygenator of blood proteins/etc. was effected. Afterwards, the system was rinsed with deionized water for 1-2 days and then dried overnight.

The dialysis membrane was kept wet at all times with saline. The dialysis membrane was flushed with normal saline, then locked with normal saline. Luer lock caps were used to preserve the filter membrane.

Zero-Bicarbonate Dialysate.

An in-vitro model was designed to develop and test a dialysate solution designed to remove bicarbonate. Freshly drawn bovine blood was used in the studied. $CO_2$ was added to the bovine blood using a MINIMAX plus hollow fiber oxygenator with a sweep gas composed of $N_2$ and $CO_2$ to simulate hypercarbic respiratory acidosis. The hypercarbic blood was pumped at blood flow rate (220 ml/min) and passed through an M10 dialysis filter with a surface area of 0.04 $m^2$. A dialysate solution including a zero concentration of bicarbonate was constituted using Stewart's physicochemical approach designed to control the strong ion difference rather than replacing bicarbonate (as described above). Hemolysis was tested by measuring pre and post-LDH levels.

The in vitro data showed successful removal of $CO_2$ from hypercarbic bovine blood using a zero-bicarbonate dialysate without causing metabolic acidosis. $CO_2$ removal was dependent on dialysate flow rate. Total $CO_2$ removal was 70-120 ml/min (30-48% of production, which is similar to mechanical ECCOR devices) at IHD (Intermittent Hemodialysis) flow rate and 4-8 ml/min (1-3%) at standard CVVHD flows. Dose response saturation occurred at 240 ml/kg/hr of dialysate flow (IHD flow rate). LDH levels decreased by mean of 22.5% (5.8% standard deviation) in post-filter blood, indicating no obvious hemolysis.

The dialysate was formed by defining the desired, post-treatment $pCO_2$ to be 50 mmHg Equation 4 was used to determine the resultant blood plasma SID, assuming $A_{tot}$ remained unchanged and $pCO_2$ reached the desire level. The dialysate SID was set to equal the determined blood plasma SID and the dialysate bicarbonate level was set to zero. The pH at the membrane interface was then determined for mixing equal amounts of dialysate and plasma using Equation 5 as described above. The dialysate composition was: 1 L of deionized water; 20 mmol of NaOH=800 mg; 112.5 mmol of NaCl=6.63 g; 3.5 mmol of KCl=261 mg; 1 mmol of MgCl=60 mg; 3 mmol of lactate=366 mg (or 0.5 ml of 50% solution in water); 0.5 mmol $NaH_2PO_4$=60 mg; and 6N HCl=1.5 ml.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of reducing the partial pressure of carbon dioxide or $pCO_2$ in blood or blood plasma during renal replacement therapy comprising:
    removing blood from a patient;
    treating the blood or blood plasma which has been separated from the blood by flowing the blood or the blood plasma on one side of at least one semi-permeable membrane, wherein carbonic anhydrase is immobilized on or in the vicinity of the at least one semi-permeable membrane, and flowing a dialysate for renal replacement therapy on the other side of the at least one semi-permeable membrane to reduce the concentration of bicarbonate in the blood or the blood plasma and reduce $pCO_2$ in the blood or the blood plasma, the dialysate having a concentration of bicarbonate less than the concentration of bicarbonate in the blood or the blood plasma before treating the blood or the blood plasma and having a composition such that the blood or the blood plasma strong ion difference that results from treating the blood or the blood plasma in conjunction with an achieved reduction in $pCO_2$ results in a blood pH or a blood plasma pH at an interface of the at least one semi-permeable membrane between 6.5 and 8.5 during treatment such that $pCO_2$ in the blood or blood plasma is reduced without inducing metabolic acidosis; and
    returning the blood or the blood plasma to the patient after treating the blood or the blood plasma on one side of the at least one semi-permeable membrane.

2. The method of claim 1 further comprising reducing the concentration of bicarbonate in the dialysate after the dialysate contacts at least one semi-permeable membrane and recycling the dialysate after reducing the concentration of bicarbonate.

3. The method of claim 1 further comprising increasing the pH of the blood or the blood plasma before the blood or the blood plasma flows on one side of the at least one semi-permeable membrane.

4. The method of claim 1 wherein the concentration of bicarbonate in the dialysate is no more than half the concentration of bicarbonate in the blood or the blood plasma before treating the blood or the blood plasma.

5. The method of claim 1 wherein the concentration of bicarbonate in the dialysate is in the range of 5 mmol and 0 mmol.

6. The method of claim 1 wherein the composition of the dialysate is determined on a per-patient basis.

7. The method of claim 6 wherein the composition of the dialysate is determined on the basis of at least one of a level of hypercarbia, a level of respiratory acidosis and a level of metabolic acidosis.

8. The method of claim 1 wherein the composition of the dialysate is determined on the basis of at least one of a patient baseline blood or blood plasma $CO_2$ concentration, a desired blood or blood plasma $CO_2$ concentration, blood or blood plasma strong ion difference and blood or blood plasma weak acid concentration.

9. The method of claim 1 further comprising determining a desired outcome level of $pCO_2$, using the following equation to determine blood or blood plasma strong ion difference or SID for the desired outcome level of $pCO_2$:

$$SID + [H^+] - \frac{K_c * pCO_2}{[H^+]} - 2 * \frac{K_c * K_3 * pCO_2}{[H^+]^2} - \frac{K_w}{[H^+]} - \frac{K_A * [A_{tot}]}{K_A + [H^+]} = 0,$$

wherein $K_w$ is the water dissociation equilibrium constant, $K_A$ is the weak acid equilibrium constant, $K_3$ is equal to $[HCO_3^-]/([W]*[CO_3^{2-}])$, $K_c$ is equal to $([H^+]*[HCO_3^-]/pCO_2)$, $A_{tot}$ is the total weak acid concentration of noncarbonated buffers, and wherein $A_{tot}$ is assumed to remain unchanged, and formulating the dialysate to have a strong ion difference approximately equal to the determined blood or blood plasma strong ion difference for the desired outcome level of $pCO_2$.

10. The method of claim 9 further comprising using the following equation to determine pH at the interface of the at least one semi-permeable membrane using the following equation:

SID={$K_c$*$pCO_2$/[H$^+$]−2*$K_c K_3$*$pCO_2$/[H$^+$]$^2$−$K_w$/[H$^+$]
$K_a$*[$A_{tot}$]/($K_a$+[H$^+$])−[H$^+$]}*(1−σ)

for mixing of equal amounts of the dialysate and the blood or the blood plasma, wherein (1−σ) is a sieving coefficient.

11. The method of claim 10 further comprising adding a buffer which does not increase bicarbonate concentration in the blood to the dialysate if the pH at the interface of the at least one semi-permeable membrane and the blood or the blood plasma is outside of a desired range.

12. The method of claim 1 wherein the blood is caused to flow on the one side of the at least one semi-permeable membrane and the blood is returned to the patient.

13. A system for reducing the partial pressure of carbon dioxide or $pCO_2$ in blood or blood plasma during renal replacement therapy comprising:
    a dialysis filter system comprising at least one semi-permeable membrane, wherein carbonic anhydrase is immobilized on or in the vicinity of the at least one semi-permeable membrane; and
    a source of a dialysate for renal replacement therapy having a concentration of bicarbonate less than the concentration of bicarbonate in the blood or blood plasma before treating the blood or the blood plasma and having a composition such that the blood or the blood plasma strong ion difference that results from treating the blood or the blood plasma in conjunction with an achieved reduction in blood or blood plasma $pCO_2$ results in a blood or a blood plasma pH at an interface of the at least one semi-permeable membrane between 6.5 and 8.5 during treatment such that $pCO_2$ in the blood or blood plasma is reduced without inducing metabolic acidosis.

14. The system of claim 13 further comprising a recycling system to reduce the concentration of bicarbonate in the dialysate after the dialysate contacts the at least one semi-permeable membrane and return the dialysate with the reduce concentration of bicarbonate to the source of dialysate.

15. The system of claim 13 further comprising a system to increase the pH of the blood or the blood plasma before the blood or the blood plasma flows on one side of the at least one semi-permeable membrane and a system to decrease the pH of the blood or the blood plasma after the blood or the blood plasma flows on one side of the at least one semi-permeable membrane.

16. The system of claim 13 wherein the concentration of bicarbonate in the dialysate is in the range of 5 mmol and 0 mmol.

* * * * *